(12) United States Patent
Brown et al.

(10) Patent No.: US 11,127,386 B2
(45) Date of Patent: Sep. 21, 2021

(54) SYSTEM AND METHOD FOR GENERATING MUSIC FROM ELECTRODERMAL ACTIVITY DATA

(71) Applicants: James S. Brown, Odessa (CA); Brian Lorne Fisher, Camden East (CA)

(72) Inventors: James S. Brown, Odessa (CA); Brian Lorne Fisher, Camden East (CA)

(*) Notice: Subject to any disclaimer, the term of this patent is extended or adjusted under 35 U.S.C. 154(b) by 0 days.

(21) Appl. No.: 16/044,140

(22) Filed: Jul. 24, 2018

(65) Prior Publication Data
US 2021/0174773 A1  Jun. 10, 2021

(51) Int. Cl.
*G10H 1/00* (2006.01)
*G01D 5/16* (2006.01)
*G01N 33/00* (2006.01)

(52) U.S. Cl.
CPC .............. *G10H 1/0066* (2013.01); *G01D 5/16* (2013.01); *G01N 33/0098* (2013.01); *G10H 2210/111* (2013.01); *G10H 2220/351* (2013.01); *G10H 2220/371* (2013.01)

(58) Field of Classification Search
CPC ........... G10H 1/0066; G10H 2220/371; G10H 2210/111; G10H 2220/351; G01D 5/16; G01N 33/0098
USPC ........................................................ 84/609
See application file for complete search history.

(56) References Cited

U.S. PATENT DOCUMENTS

| | | | | | |
|---|---|---|---|---|---|
| 4,776,323 | A | * | 10/1988 | Spector | A63B 71/0686 128/905 |
| 5,253,168 | A | * | 10/1993 | Berg | A61B 5/4857 128/905 |
| 5,768,127 | A | * | 6/1998 | Murata | G04G 21/025 700/94 |
| 6,487,817 | B2 | * | 12/2002 | Airaudi | A61B 5/05 47/1.3 |
| 6,743,164 | B2 | * | 6/2004 | Airaudi | A01G 7/00 47/1.3 |
| 6,852,919 | B2 | * | 2/2005 | Ludwig | G10H 1/00 84/735 |
| 6,933,434 | B2 | * | 8/2005 | Nishitani | G10H 1/0008 84/609 |
| 7,012,182 | B2 | * | 3/2006 | Nishitani | G10H 1/00 84/477 R |
| 7,135,637 | B2 | * | 11/2006 | Nishitani | A63B 71/0686 84/723 |

(Continued)

*Primary Examiner* — Jeffrey Donels
(74) *Attorney, Agent, or Firm* — Rick B. Yeager

(57) ABSTRACT

The Plant Choir™ system comprises a software program and hardware that measures the electrodermal activity of a person, plant, or animal and translates those readings into music on a computing device. The EDA readings of the individual subjects are translated via the software into musical notes in real time. The creation of the notes is synchronized to a master tempo in order to allow the subjects to play together in a unified fashion similar to a choir. A riff mode allows the subjects to produce multiple notes per beat. The music is rendered using a software synthesis algorithm that employs the pre-recorded sounds of real instruments. The software can also utilize MIDI devices if the operating system has that capability. The software allows the user to load and save their settings so they can create and experiment with their own choir configurations and musical scales.

16 Claims, 6 Drawing Sheets

(56) References Cited

U.S. PATENT DOCUMENTS

| | | | | |
|---|---|---|---|---|
| 7,179,984 B2* | 2/2007 | Nishitani | A63B 71/0686 | 84/600 |
| 7,183,477 B2* | 2/2007 | Nishitani | G10H 1/0066 | 84/600 |
| 7,183,480 B2* | 2/2007 | Nishitani | A63B 71/0686 | 84/609 |
| 7,298,360 B2* | 11/2007 | Howard | G06F 3/014 | 345/158 |
| 7,544,880 B2* | 6/2009 | Takai | A63B 24/0003 | 84/612 |
| 7,638,704 B2* | 12/2009 | Ludwig | G10H 1/00 | 84/672 |
| 7,781,666 B2* | 8/2010 | Nishitani | G10H 1/00 | 84/600 |
| 7,952,013 B2* | 5/2011 | Komori | A63B 71/0686 | 84/604 |
| 7,960,638 B2* | 6/2011 | Miyajima | G10H 1/0025 | 84/600 |
| 8,017,852 B2* | 9/2011 | Yamashita | G11B 27/36 | 84/600 |
| 8,022,287 B2* | 9/2011 | Yamashita | G10H 1/368 | 84/609 |
| 8,106,283 B2* | 1/2012 | Nishitani | G10H 1/00 | 84/601 |
| 8,242,344 B2* | 8/2012 | Moffatt | G10H 1/0008 | 84/609 |
| 8,269,092 B2* | 9/2012 | Terauchi | G10H 1/0025 | 84/610 |
| 8,519,250 B2* | 8/2013 | Ludwig | G10H 1/00 | 84/645 |
| 8,812,502 B2* | 8/2014 | Takatsuka | A63B 24/0084 | 707/737 |
| 2001/0015123 A1* | 8/2001 | Nishitani | A63B 71/0686 | 84/615 |
| 2002/0026746 A1* | 3/2002 | Airaudi | A61B 5/05 | 47/17 |
| 2002/0166437 A1* | 11/2002 | Nishitani | G10H 1/0008 | 84/600 |
| 2002/0170413 A1* | 11/2002 | Nishitani | G10H 1/0066 | 84/600 |
| 2003/0066413 A1* | 4/2003 | Nishitani | A63B 71/0686 | 84/615 |
| 2003/0106260 A1* | 6/2003 | Airaudi | A01G 7/00 | 47/58.1 LS |
| 2003/0167908 A1* | 9/2003 | Nishitani | A63B 71/0686 | 84/723 |
| 2004/0000225 A1* | 1/2004 | Nishitani | G10H 1/00 | 84/610 |
| 2004/0074379 A1* | 4/2004 | Ludwig | G10H 1/00 | 84/645 |
| 2004/0099129 A1* | 5/2004 | Ludwig | G10H 1/00 | 84/663 |
| 2005/0041016 A1* | 2/2005 | Howard | G06F 3/014 | 345/158 |
| 2005/0126370 A1* | 6/2005 | Takai | A63B 24/0003 | 84/636 |
| 2006/0090632 A1* | 5/2006 | Ludwig | G10H 1/00 | 84/645 |
| 2006/0111621 A1* | 5/2006 | Coppi | A61B 5/222 | 600/300 |
| 2006/0126452 A1* | 6/2006 | Yamashita | G11B 27/105 | 369/30.23 |
| 2006/0185502 A1* | 8/2006 | Nishitani | A63B 71/0686 | 84/615 |
| 2008/0288095 A1* | 11/2008 | Miyajima | G10H 1/0025 | 700/94 |
| 2009/0088877 A1* | 4/2009 | Terauchi | G10H 1/0025 | 700/94 |
| 2009/0235811 A1* | 9/2009 | Komori | A63B 71/0686 | 84/636 |
| 2009/0249945 A1* | 10/2009 | Yamashita | G10H 1/368 | 84/612 |
| 2010/0168879 A1* | 7/2010 | Takatsuka | A63B 24/0084 | 700/94 |
| 2010/0263518 A1* | 10/2010 | Nishitani | A63B 71/0686 | 84/612 |
| 2011/0022594 A1* | 1/2011 | Takatsuka | A63B 71/0622 | 707/737 |
| 2011/0093100 A1* | 4/2011 | Ramsay | G06F 3/011 | 700/94 |
| 2014/0267123 A1* | 9/2014 | Ludwig | G10H 1/00 | 345/173 |
| 2016/0198984 A1* | 7/2016 | Daniele | A61B 5/145 | 600/309 |

\* cited by examiner

SYSTEM AND METHOD FOR GENERATING MUSIC FROM ELECTRODERMAL ACTIVITY DATA

BACKGROUND—FIELD OF THE INVENTION

The present invention relates to the acquisition of electrodermal readings from one or more subjects such as persons, plants or animals for the purpose of translating those readings into music in real time. The musical notes that are selected for each of the subjects are synchronized to a master tempo setting in order to allow them to play together and create interesting harmonies similar to a choir. A riff algorithm can be employed that allows multiple notes per beat to be created for each subject in order to make the music more interesting and give it movement. The software renders the music using a synthesis algorithm that employs the pre-recorded sounds of real instruments. The software can also render sound using the MIDI programming interface provided by the operating system. The software allows the user to load and save their settings so they can create and experiment with their own choir arrangements. The user can define their own custom note sequences or scales.

BACKGROUND—PRIOR ART

Electrodermal Activity (EDA) refers to the electrical properties of the skin which are directly affected by changes in sweat gland activity of humans and animals. Psychologists have long been using EDA data to determine the responses of subjects to external stimuli such as investigative questions.

Plants produce a basic electrodermal signal that varies without any obvious external stimuli. In addition, our testing has shown that plants have a large immediate and pronounced response to warmth and the movement of warm objects around them such as animals and people. The sensitivity of the system can be adjusted to play music continuously in response to the basic signal or it can be adjusted to play music only when the plant has a more pronounced response.

SUMMARY

In one embodiment, the Plant Choir™ system comprises a software program and hardware that measures electrodermal activity of a person, plant, or animal and translates those readings into music on a computing device. The system gathers electrical activity data using proprietary Limestone Technologies DataPac_EDA™ electrodermal activity (EDA) measurement devices. The device uses an operational amplifier based circuit to apply a constant voltage across the input leads and provides an output voltage that is proportional to the current flowing through the subject and indicates the subject's resistance. The circuit has a non-linear response which allows it to sense a wide range of resistance values from 0 Ohms to tens of thousands of kilo ohms without the need for mechanical range switches. The EDA readings of the individual subjects are translated via the software into musical notes in real time. The musical notes are synchronized to a master tempo setting in order to allow the subjects to play together in an organized fashion similar to a choir. A riff algorithm may be employed to select multiple notes per beat for each subject in order to create movement and make the music more interesting. The music is rendered using a software synthesis algorithm that employs the pre-recorded sounds of real instruments. The synthesized sound is played on the system speakers. Panning controls are used to distribute the individual subject's sound among the speakers. The software can also utilize the MIDI programming interface provided by the operating system to render music using the MIDI emulation facility or through MIDI devices connected to the computer system.

The software allows the user to select program options, set music and program parameters. The software allows the user to load and save their settings so they can create and experiment with their own choir configurations. It also allows the user to create and store their own scales. Variations in the EDA signal are interpreted as notes. Each subject connected to the system is assigned to a virtual voice channel and the notes passing through the voice channels are synchronized to a master tempo setting. The voices combine to create multi part harmonies similar to a choir.

DESCRIPTION OF EMBODIMENT—PLANT CHOIR™ SYSTEM

Figure 1:
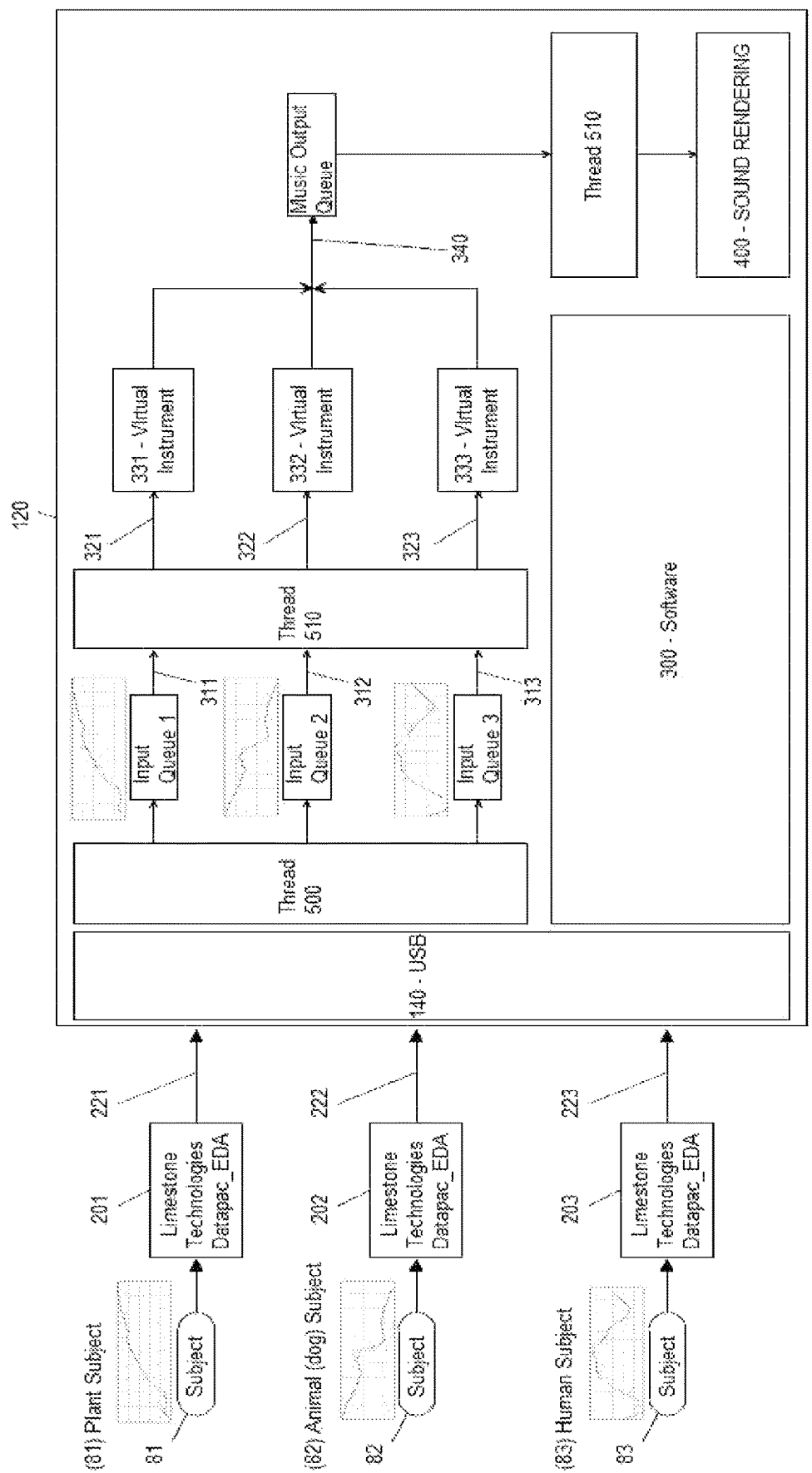
FIG. 1 is a block diagram of an embodiment of the Plant Choir hardware and software system.

FIG. 1 is a system diagram of an example embodiment of a Plant Choir™ system 100 for generating music from a plurality of subjects 81, 82, and 83. In some examples, the subjects may be plants, animals, people, or combinations thereof. In the example of FIG. 1, there are 3 subjects. In general, the system can comprise any number of one or more subjects. When one subject is used multiple sensors are attached to provide multiple data streams.

In FIG. 1, EDA devices 201, 202, and 203 are connected to subjects 81, 82, and 83 respectively. The EDA devices provide raw data steams 221, 222, and 223, respectively, to a computer 120. In this example, the data is provided through a USB (Universal Serial Bus) connection 140.

The computer runs software 300 to filter the raw data to remove noise and convert the data streams to sequences of musical notes 321, 322, and 323. The generation of the musical notes is synchronized with a master tempo setting in order to allow the subjects to play in an organized fashion. A riff algorithm may be employed to generate multiple notes per beat in order to add movement to the music to make it more interesting. In this specification, the term "musical notes" refers to individual notes or combinations of notes such as chords. The musical notes are generated according to various virtual music instruments 321, 322, and 323 which are assigned to each subject.

The computer combines the sequences of musical notes to a combined output stream 340. The output stream 340 is converted to audible music by the sound rendering module 400. The sound rendering module produces sound using a synthesis algorithm that employs pre-recorded real instrument sounds. The output is then sent to the system speakers. It is also capable of utilizing the MIDI programming interface provided by the operating system to render sound using the system MIDI emulation that drive the computer speakers or to external MIDI devices.

The software allows the user to load and save their settings so they can create and experiment with their own choir configurations. It also allows the user to create and store their own scales.

Figure 2:
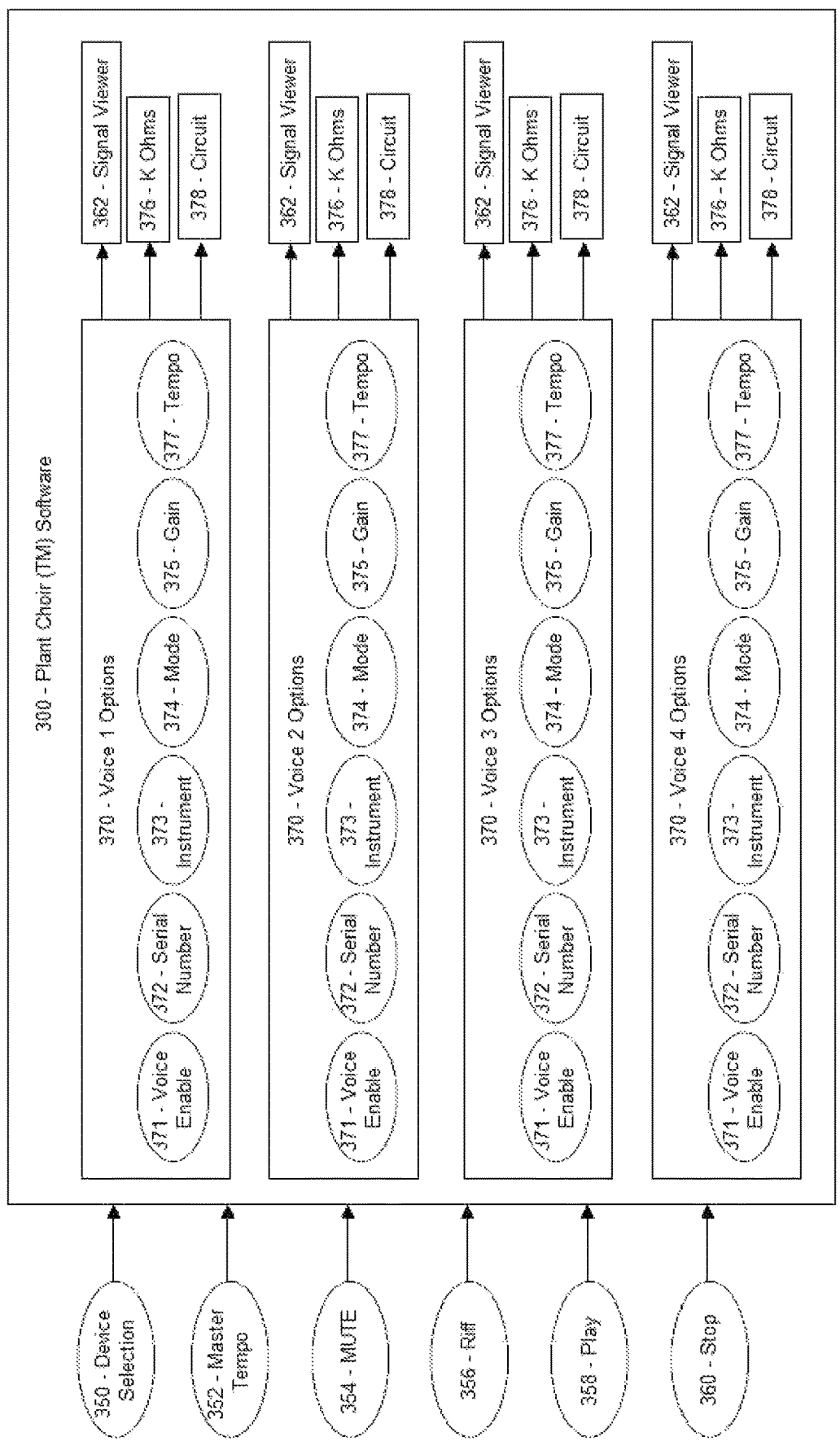
FIG. 2 is a block diagram of the Plant Choir software in the system of FIG. 1.

FIG. 2 is a block diagram of the software 300 in the Plant Choir system 100 of FIG. 1. In this embodiment, the Plant Choir software allows the user to set the following parameters:

Device Selection 350—The user may select the output method used to render the music. The default device is the Software Synthesis algorithm which ultimately drives the system speakers. The Microsoft GS Wavetable Synth (MIDI Emulation) may also be selected to render the sound on the system speakers. In addition, the operating system MIDI programming interface allows the software to render music on MIDI devices if they are installed or connected to the computer system.

Master Tempo 352—The user may determine the tempo of the notes that are produced. The production of the notes is synchronized to the master tempo setting. A checkbox is provided to disable this feature in order to allow each individual 'voice' to be assigned its own independent tempo.

Mute 354—The user may mute or silence the music playback.

Riff 356—This allows the computer to select the notes to be played in a more random fashion in order to make the melodies more interesting.

Play 358—This button or control starts the playback conversion of input into music.

Stop 360—This button or control stops the playback conversion of input into music.

Signal Viewer 362—This control is used to display the electrodermal response signal variations being produced by each individual subject.

Voice Options 370—In one embodiment, Plant Choir is able to accommodate four Limestone Technologies DataPac_EDA (electrodermal activity sensing) units. Each unit is mapped to a 'voice' in the choir for which there are independent settings and parameters:

Voice enable checkbox 371—This control enables or disables the voice from producing sound.

Serial Number 372—This control maps the voice to a specific Limestone Technologies DataPac_EDA device.

Instrument 373—This control determines the instrument that will be used to render music notes for the voice.

Mode 374—This control selects the scale or set of notes that will be used by a particular voice. In this embodiment, the following sets of notes are available: Major, Pentatonic, Chromatic, Blues, Encounters, and Percussion.

Gain 375—This control is a sensitivity value that determines when the voice will sound in response to the EDA input signal.

kohms 376—This indicator is a readout of the current resistance value of the subject between the EDA device electrodes. It is a measure of the quality of the electrical connection to the subject.

Tempo 377—If the Master Tempo enable checkbox is unchecked, then each voice is allowed to play at its own tempo. Each voice may then be assigned a different tempo in order to produce interesting rhythm combinations.

Circuit 378—Indicates the status of the circuit connecting the subject to the electrodermal activity measurement device. It is gray when there is no DataPac_EDA device assigned to the voice. It is RED when the input resistance is out of range (short or open circuit.) Is GREEN when the input resistance is within the normal operating range.

Setup and Operation

Figure 3:
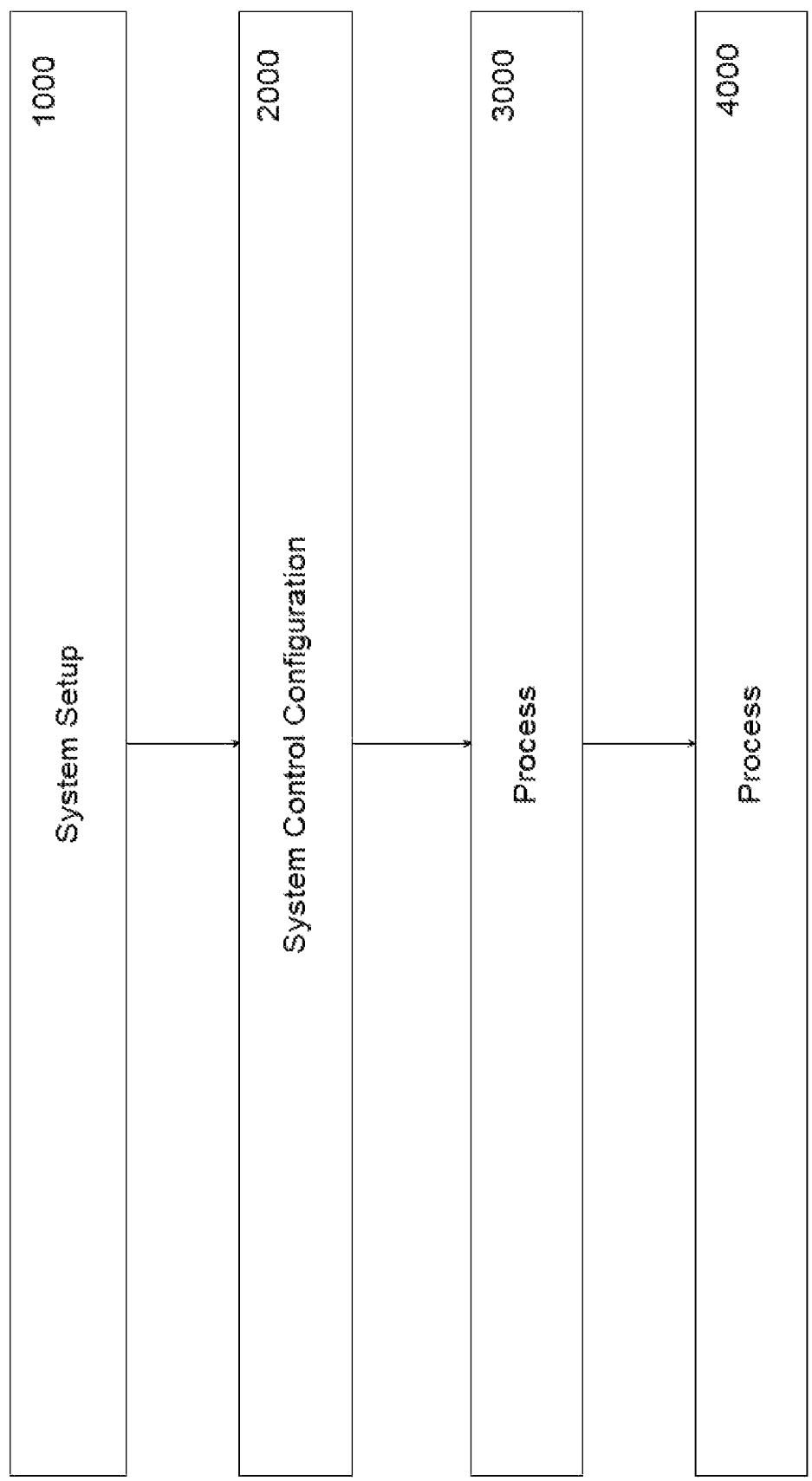
FIG. 3 is a flow diagram of an example setup and control for the system of FIG. 1.

FIG. 3 is a flow diagram of an example setup and control for the system of FIG. 1.

At Step 1000, the system is setup. EDA devices 201, 202, and 203 are connected to individual subjects 81, 82, and 83. Each EDA device 201, 202, and 203 is connected to the computer 120.

At Step 2000, the system controls are configured by the user. The user selects, or the system defaults to, an output device selection 350, master tempo 352, riff 356. During operation, the user may select play 358, stop 360, mute 354, and signal viewer 362. The user selects, or the system defaults to, voice options 370 for each subject.

At Step 3000, the system acquires EDA data and translates it into music.

Figure 4:
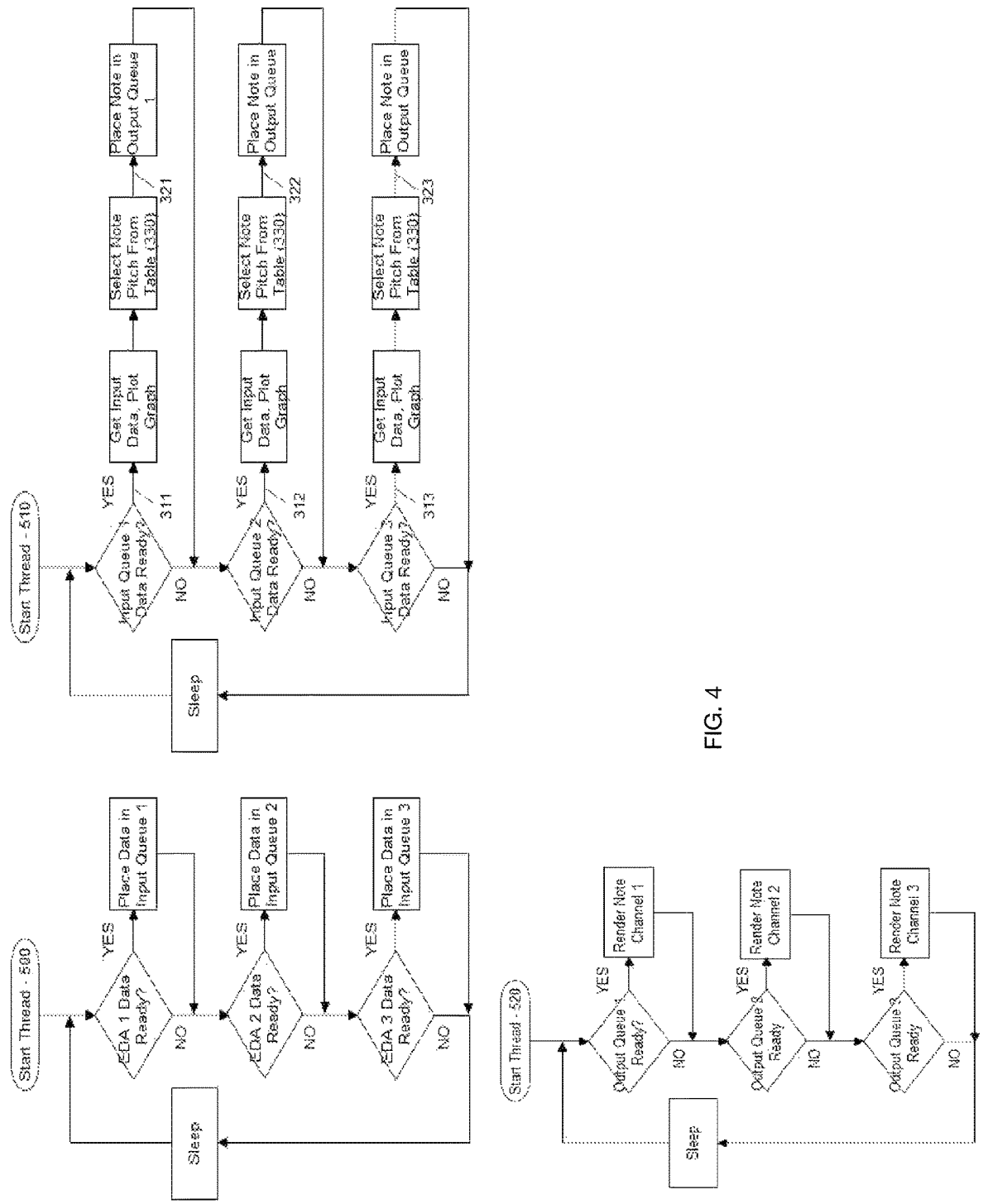
FIG. 4 is a software and logic diagram of FIG. 1.

FIG. 4 is a software logic diagram for the system of FIG. 1. A background thread 500 running within the Plant Choir software gathers data from the DataPac_USB devices as the data becomes available and places the data in its respective Input Queue.

A second thread running 510 within the Plant Choir software is responsible for removing samples from the Input Queue and translating those values into musical notes through the use of a lookup table 530.

The software normalizes each input signal 311, 312, 313 to automatically compensate for changes in the input signal amplitude. The normalized input values are used to select notes 321, 322, and 323 from a lookup table 330. The lookup table assigned to each 'voice" is configurable within the software and may contain note pitch values for a variety of musical modes such as major, minor, chromatic, pentatonic, blues, percussion, and custom subsets, for example. The software user can also define their own custom scales or musical modes.

A note structure is created which contains information such as pitch, tempo, volume, instrument, and effects. Once the parameters of the note have been determined, the note structure is placed in an Output Queue to await rendering by the Render Music module as sound.

At step 4000, the individual musical notes are combined and played as an audible concert.

A third thread 520 running within Plant Choir is responsible for removing notes from the Output Queue and rendering them using a synthesis algorithm that employs the pre-recorded sounds of real instruments. The sound is output on the system speakers.

As an alternative the software can also render sound through the operating system's MIDI programming interface that provides a MIDI emulation using the system sound card that can be played on the system speakers, or through MIDI devices attached to the computer system.

In this embodiment, a system of software and proprietary hardware is used to acquire EDA readings from one or more subjects in order to produce musical notes that are synchronized to a master tempo to allow the subjects to play together and create music in multi-part harmony in a fashion similar to a choir. It is also possible to attach multiple EDA devices to different parts of a single subject and use that data to drive multiple voices.

Each DataPac_EDA device samples the subject's surface resistance at fixed intervals and transmits the readings to a personal computer via a USB (Universal Serial Bus) connection. One DataPac_EDA device is used per subject and multiple DataPac_EDA devices may be used to connect multiple subjects to the personal computer system. Multiple EDA devices can be attached to different parts of a single subject in order to drive multiple voices.

Figure 5:
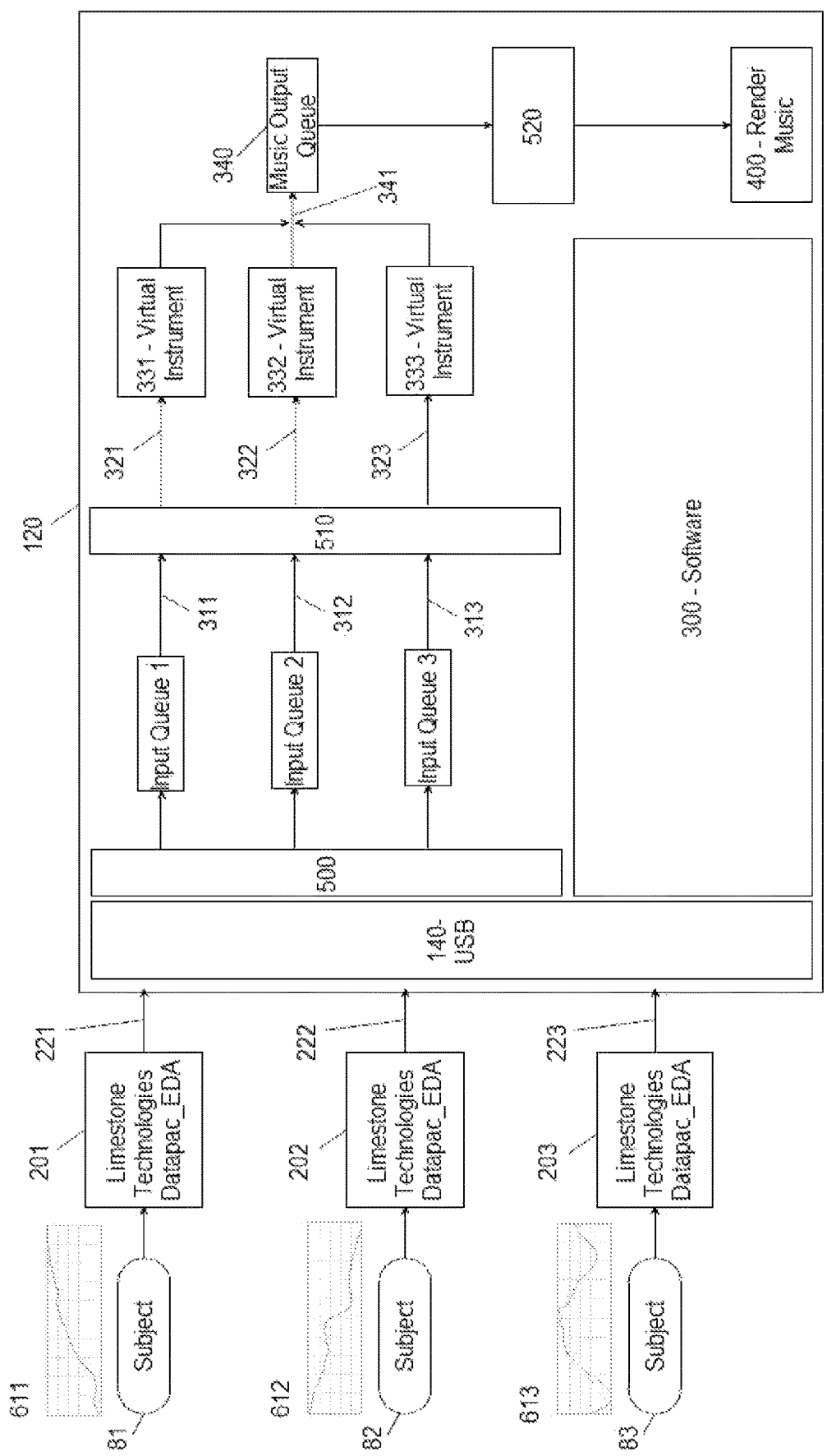
FIG. 5 is an example detailed block diagram of an embodiment of the Plant Choir hardware and software system.

FIG. 5 is an example detailed block diagram of an embodiment of the Plant Choir hardware and software system. In this example, subject 81 is a plant with an example input EDA waveform 611; subject 82 is a dog with an example input EDA waveform 612; and subject 83 is a human with an example input EDA waveform 613. Background thread 500 gathers the EDA data from the EDA devices for each subject and places the data in the respective input queues 311, 312, and 313. Second thread 510 removes the EDA data from the Input Queues and translates those values into musical notes through the use of a lookup table 530 (not shown). Third thread 520 removes the combined notes from Music Output Queue 340 and feeds the notes to the Render Music module 400 that uses the sound synthesis algorithm or the operating system MIDI programming interface to render the music.

Figure 6:
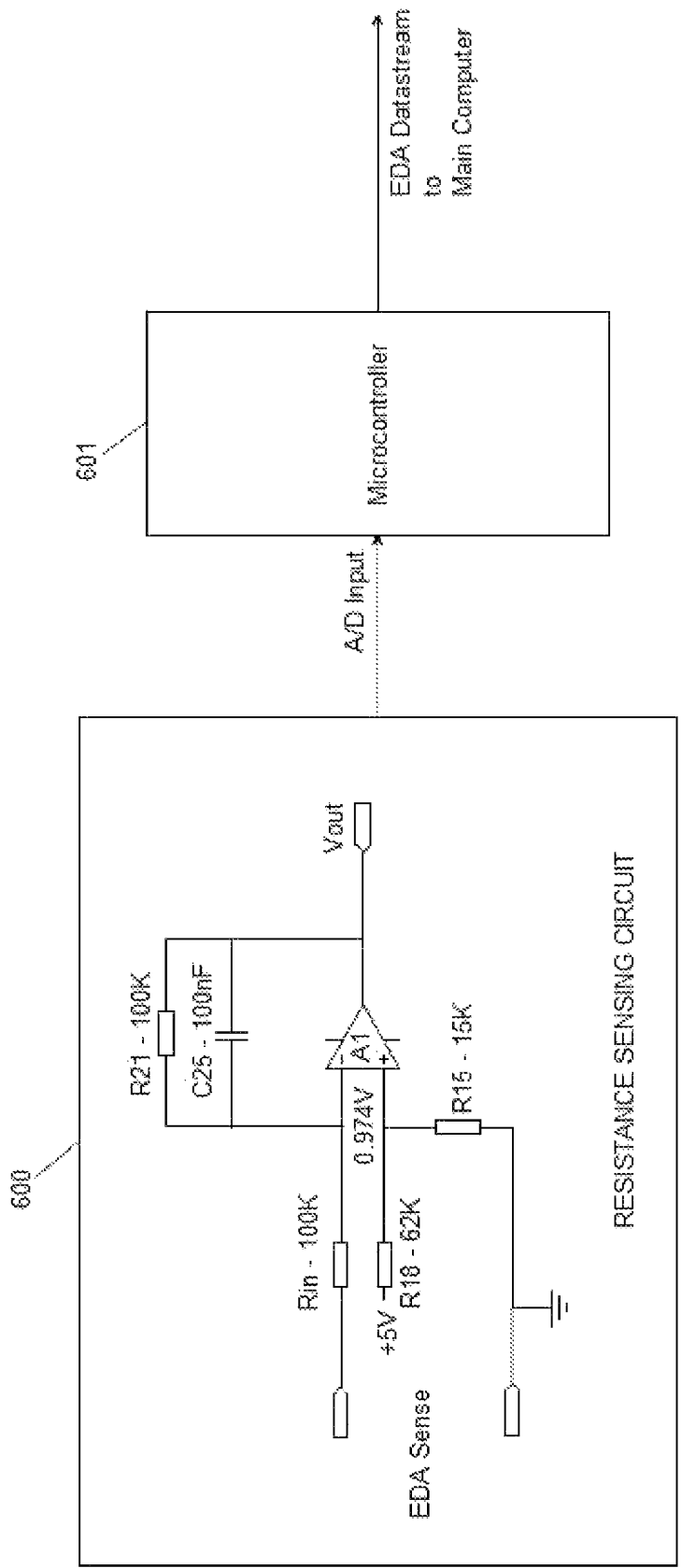
FIG. 6 is the resistance sensing circuit and block diagram of the proprietary electrodermal activity sensing device.

FIG. 6 is a circuit and block diagram that illustrates the internal workings of the Limestone Technologies Datapac_USB electrodermal activity device. The resistance sensing circuit 600 uses an operational amplifier A1 to apply a constant 0,974 volts across the input leads. The voltage is determined by the resistor divider circuit comprised of R18 and R15. This voltage is applied to the positive input of the operational (op) amplifier (amp). The voltage difference between the positive and negative inputs of the op amp is assumed to be zero to facilitate circuit analysis. The op amp will keep the voltage at the negative input equal to the voltage at the positive input by applying Vout to the voltage divider consisting of R21, Rin and EDA Sense. Vout can be calculated as ((R21/(EDASense+Rin))+1)*0.974.

The Resistance Sensing Circuit 600 has a non-linear response to the subject's resistance (EDA Sense) that allows it to respond to values in the range of 0 ohms to tens of thousands of kilo ohms without the need for range switching.

Vout is applied to the A/D input of the microcontroller 601. The software in the microcontroller is responsible for taking samples at fixed intervals and transmitting them to the main computer through the USB interface.

Rin is used to protect the op amp A1 when the input leads are shorted together. The maximum current through the leads is 9.75 micro amps.

It is to be understood that the specific embodiments and examples described above are by way of illustration, and not limitation. Various modifications may be made by one of ordinary skill, and the scope of the invention is defined in the appended claims.

What is claimed is:

1. A system for generating music from the electrodermal activity data of a plurality of subjects, the system comprising
a computing device comprising
software that converts EDA data to musical notes by converting variations in an EDA signal from each of multiple subjects to musical notes, and
synchronizing musical notes from the multiple subjects to a master tempo setting;
a plurality of EDA devices, each EDA device configured to acquire electrodermal activity data from a subject, each electrodermal activity device comprising
a pair of input leads configured to be attached to a subject,
a resistance sensing circuit configured to provide a constant voltage across the first pair of input leads and to provide a non-linear response to the electrodermal resistance of the subject, the resistance sensing circuit comprising
an operational amplifier circuit configured to apply a constant voltage across the first pair of input leads and to provide an output voltage that is proportional to current flowing through the subject, and
a microcontroller configured to take samples and transmitting data to the computing device; and
a sound rendering module.

2. The system of claim 1 wherein the connection between each EDA device and the computing device is a Universal Serial Bus connection.

3. The system of claim 1 wherein the connection between each EDA device and the computing device is a wireless connection.

4. The system of claim 1 wherein the plurality of subjects are plants.

5. The system of claim 1 wherein the plurality of subjects are animals.

6. The system of claim 1 wherein the plurality of subjects are persons.

7. The system of claim 1 wherein the plurality of subjects further comprise combinations of plants, animals, or persons.

8. The system of claim 1 wherein the an operational amplifier circuit further comprises
a constant positive voltage input, and
a negative voltage input, such that the operational amplifier is configured to maintain the negative voltage input equal to the voltage at the positive input by applying an output voltage to a voltage divider.

9. The system of claim 1 wherein the computing device further comprises software that
employs a riff algorithm to assign multiple notes per beat for each of the multiple subjects.

10. The system of claim 1 wherein the sound rendering module further comprises system speakers; and
software renders the music using a synthesis algorithm that direct pre-recorded sounds of real instruments to the system speakers.

11. The system of claim 1 wherein the sound rendering module further comprises
an MIDI programming interface configured to render sound using MIDI emulation that drives speakers or external MIDI devices.

12. The system of claim 1 wherein the computing device further comprises software that
permits a user to load and save settings in order to create and experiment with choir configurations.

13. The system of claim 1 wherein the computing device further comprises software that
permits a user to create and store scales.

14. A system for generating music from the electrodermal activity data of a first subject, the system comprising
a first electrodermal activity device comprising
a first pair of input leads configured to be attached to the first subject, a resistance sensing circuit configured to provide a constant voltage across the first pair of input leads and to provide a non-linear response to the electrodermal resistance of the first subject, the resistance sensing circuit comprising
   an operational amplifier circuit configured to apply a constant voltage across the first pair of input leads and to provide an output voltage that is proportional to the current flowing through the first subject, and
   a microcontroller configured to take samples and transmitting data to the computing device;
a computing device comprising software that converts EDA data to musical notes by
   converting variations in an EDA signal from each of multiple subjects to musical notes, and
   synchronizing musical notes from the multiple subjects to a master tempo setting ; and
a sound rendering module.

15. The system of claim 14 wherein the the microcontroller is configured to transmit data to the computing device through a USB interface.

16. The system of claim 14 further comprising a second electrodermal activity device comprising
   a second pair of input leads configured to be attached to the first subject at a different location than the first pair of input leads,
   a resistance sensing circuit configured to provide a constant voltage across the second pair of input leads and to provide a non-linear response to the electrodermal resistance of the first subject, the resistance sensing circuit comprising
      an operational amplifier having a constant positive voltage input and a negative voltage input, such that the operational amplifier is configured to maintain the negative voltage input equal to the voltage at the positive input by applying an output voltage to a voltage divider, and
   a microcontroller configured to take samples and transmitting data to the computing device.

* * * * *